United States Patent [19]

Kollonitsch

[11] 3,956,367

[45] May 11, 1976

[54] 3-FLUORO-D-ALANINE AND PHARMACOLOGICALLY ACCEPTABLE ESTERS, AND PHARMACOLOGICALLY ACCEPTABLE SALTS THEREOF

[75] Inventor: Janos Kollonitsch, Westfield, N.J.

[73] Assignee: Merck & Co., Inc., Rahway, N.J.

[22] Filed: Aug. 5, 1974

[21] Appl. No.: 494,945

Related U.S. Application Data

[63] Continuation-in-part of Ser. No. 223,354, Feb. 3, 1972, and a continuation-in-part of Ser. No. 245,288, April 18, 1972, Pat. No. 3,839,170, which is a continuation of Ser. No. 60,645, Aug. 3, 1970, abandoned.

[52] U.S. Cl. .................. 260/482 R; 204/158 R; 260/534 C; 424/311; 424/319
[51] Int. Cl.² .............. C07C 101/10; C07C 101/18; C07C 101/19
[58] Field of Search .................. 260/482 R, 534 C

[56] References Cited
FOREIGN PATENTS OR APPLICATIONS
39-30152  12/1964  Japan .............................. 260/534 C

OTHER PUBLICATIONS

Yiian et al., Chemical Abstracts, Vol. 54, (1960), 12096i to 12097f.

Lettre et al., Chemical Abstracts, Vol. 68, (1968), 22229n.

*Primary Examiner*—Richard L. Raymond
*Attorney, Agent, or Firm*—Hesna J. Pfeiffer; Henry H. Bassford; Julian S. Levitt

[57] ABSTRACT

3-Fluoro-D-alanine, its pharmacologically acceptable esters, and pharmacologically acceptable salts of the foregoing, as well as other pharmacologically acceptable derivatives of 3-fluoro-D-alanine which, when administered clinically, are effective in releasing 3-fluoro-D-alanine in vivo, are potent antibacterial agents, and are prepared by fluorination of D-alanine with fluoroxyperfluoroalkanes or fluoroxypentasulfur in the presence of a free radical initiator followed by esterification and/or treatment with acids or bases.

8 Claims, No Drawings

3-FLUORO-D-ALANINE AND PHARMACOLOGICALLY ACCEPTABLE ESTERS, AND PHARMACOLOGICALLY ACCEPTABLE SALTS THEREOF

This a continuation-in-part of applications Ser. No. 223,354, filed Feb. 3, 1972 and Ser. No. 245,288, filed April 18, 1972 now U.S. Pat. No. 3,839,170, which, in turn is a continuation of application Ser. No. 60,645, filed Aug. 3, 1970, now abandoned.

This invention relates to a novel process for fluorination of organic compounds, and to new fluorinated compounds so prepared. In particular it relates to the fluorination of organic compounds in the liquid or solid phase with fluoroxyperfluoroalkanes or fluoroxypentafluorosulfur. Still more particularly it relates to mono- or poly-fluorination or organic compounds with fluoroxyperfluoroalkanes or fluoroxypentafluorosulfur under conditions conducive to the formation of free radicals.

A preferred embodiment of this invention is the novel compound, 3-fluoro-D-alanine, which is produced when D-alanine is fluorinated in accordance with this novel fluorination process. This novel 3-fluoro-D-alanine and its pharmacologically acceptable esters, and pharmacologically acceptable salts thereof, display potent antibacterial activity against several classes of pathogenic microorganisms.

The novel process of this invention can be represented by the following equation:

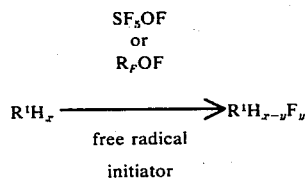

$R^1H_x$ represents an organic molecule having $x$ replaceable hydrogens linked to carbon. The organic molecule substrate can be virtually any such entity which is subject to free radical substitution and includes such as: (1) mono- and polynuclear carbocyclic aromatic compounds such as benzenes, naphthalenes, phenanthrenes, anthracenes, fluoroanthenes, pyrenes, chrysenes, indenes, fluorenes, napthacenes and the like, either unsubstituted or substituted with such as halo, lower alkyl, lower alkoxy, amino, or mono- or di-(lower alkyl)amino; (2) mono- or polynuclear alicyclic compounds, such as the monocycloalkanes, poly- and perhydronapthalenes, poly- and perhydrophenanthrenes, adamantane and the like, either unsubstituted or substituted with such as lower alkyl, amino, carboxyl, nitro, halo or lower alkoxy; (3) alkanes and alkenes either unsubstituted or substituted with such as halo, or amino; (4) amino acids, either cyclic or acyclic, and either basic or acidic; (5) fatty acids and derivatives such as amides, either unsubstituted or substituted with such as halo; (6) polymers such as polycaprolactam, polyethylene, polystyrene and the like; (7) heterocycles, either substituted or unsubstituted such as cinnolines, phthalazines, quinazolines, quinoxalines, acridines, phenanthridines, phenantholines, phenazines, pyridazines, imidazoles, pyrazoles, indoles, triazoles, indazoles, pyrroles, furans, thiophenes, piperidines, piperazines, pyrrolidines, azetidines, and the like.

$R_fOF$ represents a fluoroxyperfluoroalkane wherein the alkyl group is of 1 to about 5 carbon atoms, such as fluoroxytrifluoromethane, fluoroxyperfluoroethane, 1- or 2-fluoroxyperfluoropropane, or 2-fluoroxyperfluoro-2-methylpropane.

Prior to this invention the scope and utility of known methods for substitutive fluorination of organic compounds in the sense of the equation:

RH → RF were very limited. The most important methods available for the above type of transformation were (1) reaction with elementary fluorine, (2) electrolytic fluorination in liquid hydrogen fluoride, (3) reaction with high valency oxidative metallic fluorides such as cobalt trifluoride, (4) reaction with perchloryl fluoride, and (5) fluorination with fluoroxyperfluoroalkanes.

The main limitations with methods (1), (2) and (3) are that they usually result in mixtures of polyfluorinated compounds even in the case of substrates with simple structures. With more complex substrates, extensive degradation and carbon skeletal rearrangements often occur, thus severely limiting the yield and predictability of any individual product. In contrast, method (4), employing perchloryl fluoride, allows more selective fluorination, and does not generally cause degradation of the substrate, but is only effective with especially reactive substrates such as activated methylene groups.

Method (5), fluorination with fluoroxyperfluoroalkanes has been reported in the prior art. D. H. R. Barton et al., in Chemical Communications, 1968, 804, 806; 1969, 227 published on the fluorination of alkenes and aromatic compounds. The reactions described therein were electrophilic, proceeded in the "dark", i.e., in the absence of irradiation, and required "suitably activated" aromatic substrates. Allison et al. in J. Amer. Chem. Soc., 81, 1089–1091 (1959) also reported on "Reactions of Trifluormethyl Hypofluorite with Organic Compounds". The reactions described were conducted at room temperature in the gas phase and were spontaneous or initiated with ultraviolet light or by a spark. In the case of alkenes, the fluoroxytrifluoromethane added across the double bond; benzene exploded to give a very low yield of fluorobenzene; and alkanes yielded the entire spectrum of fluorinated alkanes in low yield.

Surprisingly it has now been found that the limited usefulness of fluoroxyperfluoroalkanes and fluoroxypentafluorosulfur can be greatly extended by conducting the reaction in the liquid or solid phase under conditions conducive to the formation of free radicals.

The novel process of this invention comprises treating the substrate with a fluoroxyperfluoroalkane or fluoroxypentafluorosulfur under the influence of a free radical initiator such as light which includes ultraviolet light, ionizing radiations such as γ-rays or microwaves, or chemical chain initiators such as azo compounds, for example, azo-bis-isobutyronitrile or combinations of such free radical initiators. The preferred mode of operation is to dissolve the substrate in a suitable solvent which is inert to the fluorination reaction such as fluorotrichloromethane or other similar halogenated alkane, or a strong acid such as liquid hydrogen fluoride, fluorosulfonic acid, trifluoroacetic acid or sulfuric acid; expose the solution to the free radical initiator; with vigorous stirring and maintenance of temperature, admit the required amount of the fluoroxy reagent slowly to the reaction mixture; and continue agitation and irradiation until reaction is complete.

Use of one of the strong acids as solvent is particularly advantageous in, but not limited to, those instances wherein the substrate carries one or more basic functional groups such as amino, or alcohol or the like. In addition, if desired, a strong acid can be employed in combination with one of the non-acidic solvents.

Because of the low boiling point of the reagents it is convenient to conduct the reaction at temperatures as low as −80°C. in which case the reaction proceeds at atmospheric pressure.

A suitable reaction vessel for atmospheric pressure reactions is one machined from a Kel-F rod equipped with an ultraviolet-transparent window. Alternatively the reaction can be conducted in a pressure vessel such as a Hastelloy bomb or a steel bomb with a platinum lining, in which case higher temperatures, for instance up to about 100°C. can be employed. In such case the use of γ-rays or x-rays as free radical initiator is convenient, as these high energy rays penetrate the wall of the reactor.

The above described process can be performed by conventional batch techniques, or alternatively it can be run in a continuous manner in a tubular reactor either with or without packing such as Raschig rings, saddles or the like through which the substrate or its solution and the fluorinating agent are pumped, preferably in a countercurrent fashion while being exposed to radical generating radiation. This method of operation is particularly advantageous in cases where the particular substrate is subject to reaction with the fluoroxy compound even in the absence of radical generating conditions. In this case, by employing the above continuous technique it becomes possible to accelerate the radical type reaction, while leaving unchanged the rate of the non-radical reaction, thus raising the yield of the product formed by radical reaction.

A convenient source of radiation for radical generation was found to be a Hanovia mercury-xenon arc lamp No. 9778-1, run by a 1000 W. power supply. The lamp was mounted in a Schoeffel IH 15 1-N Projector equipped with a quartz condensor lens and a heat filter (water).

The novel process of this invention provides a convenient route to a large variety of organic fluorine compounds. Such compounds are known to have wide ranging utility as, for example, solvents, intermediates in organic synthesis, insecticides, plant growth regulators, herbicides, refrigerants, lubricants, pharmaceuticals and so on. 5-Fluoro-2-methyl-1-(p-methylsulfinylbenzylidene)-inden-3-acetic acid and 4-(2-pheny-1,1,2,2-1-tetrafluoroethyl)-α,α-dimethylbenzylamine prepared by the novel process of this invention have utility as antiinflamatory and antiarrhythmic agents respectively.

In addition the novel process provides a useful route to many new compounds and new compositions of matter such as 3-fluoro-D-alanine, a compound displaying antibacterial activity against several classes of pathogenic microorganisms. This 3-fluoro-D-alanine and its pharmacologically acceptble esters, which are conveniently prepared by reacting 3-fluoro-D-alanine with the corresponding alcohol in the presence of an acidic catalyst, as for example the alkyl esters, and particularly the lower alkyl esters such as methyl 3-fluoro-D-alaninate, ethyl 3-fluoro-D-alaninate, propyl 3-fluoro-D-alaninate, substituted-alkyl esters such as pivaloyloxymethyl-3-fluoro-D-alaninate, aralkyl esters such as benzyl 3-fluoro-D-alaninate, cycloalkyl esters, such as cyclohexyl 3-fluoro-D-alaninate, cyclopentyl 3-fluoro-D-alaninate and the like; pharmacologically acceptable salts of the foregoing such as 3-fluoro-D-alaninate hydrohalide, 3-fluoro-D-alanine hydrochloride, methyl 3-fluoro-D-alaninate hydrochloride, sodium 3-fluoro-D-alaninate, calcium 3-fluoro-D-alaninate, potassium 3-fluoro-D-alaninate, and the like; as well as other pharmacologically acceptable carboxy-substituted and N-substituted-derivatives of 3-fluoro-D-alanine which, when administered to a live mammal, are effective in releasing 3-fluoro-D-alanine in vivo; are potent antibacterial agents, and are useful in inhibiting the growth of pathogenic bacteria of both gram positive and gram negative genera such as Streptococcus, Escherichia, Staphylococcus, Salmonella, Pseudomonas, Diplococcus, Klebsiells, Proteus, Mycobacterium, Vibrio and Pasteurella and more particularly the species *Escherichia coli*, *Salmonella schottmuelleri*, *Proteus vulgaris*, *Proteus mirabilis*, *Pseudomonas aeruginosa*, *Staphylococcus aureus* and *Streptococcus pyogenes*.

The carboxy-substituted and N-substituted derivatives of 3-fluoro-D-alanine, and in particular alkyl esters such as methyl, ethyl, propyl or butyl esters, cycloalkyl esters, and aralkyl esters such as the benzyl esters are also valuable intermediates, wherein the said substituents serve as carboxyl protecting groups and/or amino-protecting groups.

The presently invented 3-fluoro-D-alanine antibacterial compositions, containing 3-fluoro-D-alanine, its pharmacologically acceptable esters, and pharmacologically acceptable salts of the foregoing, as well as other pharmacologically acceptable derivatives of 3-fluoro-D-alanine effective in releasing 3-fluoro-D-alanine in vivo, are ordinarily administered in the form of a pharmaceutical composition containing the 3-fluoro-D-alanine compound in combination with a pharmacologically acceptable solid or liquid carrier, and are prepared for administration in convenient dosage form such as pills, tablets, capsules, syrups for oral use, or in a liquid form adapted for administration of antibacterial compounds by injection.

The following examples illustrate methods of carrying out the present invention, but it is to be understood that these examples are given for purposes of illustration and not of limitation.

EXAMPLE 1

3-Fluoro-D-alanine

Into a solution of 1.822 g. of D(-) alanine in 45 ml. of liquid HF, 0.6 g. of fluoroxytrifluoromethane gas was passed over a period of about 1 hour while being magnetically stirred, cooled in a dry-ice-acetone bath and irradiated by ultraviolet light. After 80 minutes further ultraviolet irradiation, 2 g. more of fluoroxytrifluoromethane gas was passed in while being ultraviolet irradiated over 1½ hours, followed by another 1 hour ultraviolet irradiation.

The solvent was removed by blowing through it a stream of nitrogen gas. The residue was dissolved in ice-water and a sample of it was analyzed in the Spinco-Beckman amino acid analyzer, indicating a 41% yield of 3-fluoro-D-alanine, and 32% of unreacted starting material. For isolation, the mixture was chromatographed on Dowex 50 × 8 cation exchange resin ($H^+$ form) (a polystyrene nuclear sulfonic acid resin sold by Dow Chemical Co., Midland, Michigan). For elution, 2N HCl was employed. From the appropriate fractions, by evaporation in vacuo, pure 3-fluoro-D-alanine hydrochloride was obtained. 3-Fluoro-D-alanine was liberated from the hydrochloride in water-pyridine-isopropanol mixture, m.p. 166°–168°C. (dec.); $[\alpha]_D$, –9.3° (1N-HCl).

EXAMPLE 2

About 0.2 g. of 3-fluoro-D-alanine was suspended in 10 ml. of methanol, and the suspension was saturated with hydrogen chloride gas, without cooling. The resulting mixture was allowed to stand at room temperature for a period of about 20 hours, at the end of which time the resulting solution was evaporated to dryness in vacuo. The residual material was crystallized from 3 ml. of isopropanol to give approximately 0.14 g. of methyl 3-fluoro-D-alaninate hydrochloride in the form of colorless crystals; m.p. 128°–129°C. (dec.). Treatment of this methyl 3-fluoro-D-alaninate hydrochloride with an aqueous-pyridine-isopropanol mixture gives methyl 3-fluoro-D-alaninite.

In accordance with the foregoing procedure, but employing ethanol in place of methanol, there is obtained ethyl 3-fluoro-D-alaninate hydrochloride; treatment of this hydrochloride salt with aqueous-pyridine-isopropanol mixture, gives ethyl 3-fluoro-D-alaninate.

Similarly, when propanol is employed in place of methanol in the foregoing procedure, there is obtained propyl 3-fluoro-D-alaninate hydrochloride; treatment of this hydrochloride salt with aqueous-pyridine-isopropanol mixture gives propyl 3-fluoro-D-alaninate.

EXAMPLE 3

A mixture of 10.7 g. of 3-fluoro-D-alanine, 19.5 g. p-toluene sulfonic acid monohydrate, 50 ml. benzyl alcohol and 20 ml. benzene are heated at reflux temperature for a period of about 5 hours in an apparatus which continuously removes water formed in the reaction. The reaction solution is cooled, diluted with 200 ml. of ether, and the crystalline material which precipitates is recovered by filtration, washed with ether and dried to give about 10 g. of benzyl 3-fluoro-D-alaninate p-toluenesulfonate. Treatment of this benzyl 3-fluoro-D-alaninate p-toluenesulfonate with an aqueous-pyridine-isopropanol mixture gives benzyl 3-fluoro-D-alaninate.

Various changes and modifications may be made in carrying out the present invention without departing from the spirit and scope thereof. Insofar as these changes and modifications are within the purview of the annexed claims, they are to be considered as part of this invention.

What is claimed is:

1. A compound selected from the group consisting of 3-fluoro-D-alanine substantially free of the L-form, and its pharmacologically acceptable lower alkyl, pivaloyloxymethyl, benzyl, cyclohexyl and cyclopentyl esters; and pharmacologically acceptable salts thereof.

2. 3-Fluoro-D-alanine substantially free of the L-form.

3. A compound as defined in claim 1 having the chemical name 3-fluoro-D-alanine hydrohalide.

4. 3-Fluoro-D-alanine hydrochloride substantially free of the L-form.

5. A pharmacologically acceptable ester of 3-fluoro-D-alanine substantially free of the L-form having the following formula:

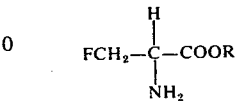

wherein R is lower alkyl, cyclohexyl, cyclopentyl or benzyl.

6. Methyl 3-fluoro-D-alaninate substantially free of the L-form.

7. Methyl 3-fluoro-D-alaninate hydrochloride substantially free of the L-form.

8. Ethyl 3-fluoro-D-alaninate substantially free of the L-form.

* * * * *